US012156951B2

(12) United States Patent
Saylik et al.

(10) Patent No.: US 12,156,951 B2
(45) Date of Patent: Dec. 3, 2024

(54) SYSTEM AND METHOD FOR DISINFECTING FUEL TANKS

(71) Applicant: The Boeing Company, Chicago, IL (US)

(72) Inventors: Murat Saylik, Oklahoma City, OK (US); Joseph Andrew Bolton, Dubuque, IA (US)

(73) Assignee: THE BOEING COMPANY, Arlington, VA (US)

( * ) Notice: Subject to any disclaimer, the term of this patent is extended or adjusted under 35 U.S.C. 154(b) by 380 days.

(21) Appl. No.: 16/879,211

(22) Filed: May 20, 2020

(65) Prior Publication Data

US 2021/0361790 A1    Nov. 25, 2021

(51) Int. Cl.
 *A61L 2/10* (2006.01)
 *A61L 2/26* (2006.01)

(52) U.S. Cl.
 CPC .................. *A61L 2/10* (2013.01); *A61L 2/26* (2013.01); *A61L 2202/11* (2013.01); *A61L 2202/14* (2013.01); *A61L 2202/23* (2013.01)

(58) Field of Classification Search
 CPC ..................................... A61L 2/20; A61L 2/10
 See application file for complete search history.

(56) References Cited

U.S. PATENT DOCUMENTS

| 8,894,925 | B2 | 11/2014 | Parfitt et al. |
| 9,034,252 | B2 | 5/2015 | Smith |
| 2008/0199353 | A1* | 8/2008 | Mlodzinski ............. G07F 11/62 422/186 |
| 2014/0084179 | A1 | 3/2014 | Ben-Hur et al. |
| 2016/0331856 | A1* | 11/2016 | Smith ........................ A61L 2/10 |
| 2019/0030195 | A1* | 1/2019 | Hatti ......................... A61L 2/24 |
| 2020/0017351 | A1* | 1/2020 | Schultz ................... B67D 7/365 |

FOREIGN PATENT DOCUMENTS

WO    WO-9733629 A1 *  9/1997  ............ A61L 2/0011

* cited by examiner

*Primary Examiner* — Kevin Joyner
(74) *Attorney, Agent, or Firm* — MH2 Technology Law Group LLP

(57) ABSTRACT

A fuel tank disinfection system, including one or more ultraviolet (UV) light emitters disposed within a fuel tank and configured to irradiate one or more water collecting areas within the fuel tank with UV light; and one or more UV light sensors disposed within the fuel tank and in proximity to the one or more water collecting areas and configured to measure the UV light irradiated on the one or more water collecting areas.

21 Claims, 7 Drawing Sheets

SYSTEM AND METHOD FOR DISINFECTING FUEL TANKS

TECHNICAL FIELD

The present disclosure generally relates to reducing microbial contamination of fuel tanks, and more particular, to a system and method for disinfecting fuel tanks.

BACKGROUND

Fuel tanks installed in crafts, such as aircrafts, do not operate in sterile environments. Instead, both the fuel tanks and the fuel contained therein are routinely exposed to air during their operating life-cycle. Accordingly, both may become contaminated with microorganisms naturally present in the environment. Such microorganisms can include bacteria, molds, virus, and fungi. In addition, water is known to collect in fuel tanks both from the humidity naturally present in the air and through water introduced with the fuel.

These microorganisms are known to thrive in the presence of water, and particularly, at the interface of fuel and water. These fuel/water interfaces exist in minute quantities throughout the fuel tank. However, in locations where water can collect and be trapped in significant amounts, the fuel/water interface has a significantly higher water volume that may support a concentration of microorganism growth which would be orders of magnitude larger than anywhere else in the fuel tank. Microbial growth contamination can clog fuel filters and sensors inside the fuel tank. In addition, some microorganisms produce acid as a by-product of their growth, and this acid may be concentrated in water collecting areas where the microbe's growth is concentrated. Accordingly, acid from microbial growth contamination can cause corrosion and damage to the fuel tank structure, especially in water collecting areas. Craft, such as aircraft, maintained with fuel in the fuel tanks in hot and humid environments and/or for extended periods of time may be particularly susceptible.

Current methods for reducing microbial contamination in fuel tanks involve maintaining a full level of fuel in the fuel tanks to displace humid air and defueling before operation to a desired fuel level, periodic (weekly) draining of water from the fuel tanks and testing (annually) for microbial presence, and/or pre-treatment and disinfection of fuel coming into the fuel tank to reduce an amount of water or microbes present in the fuel. In addition, fuel tanks have to be regularly inspected for corrosion, involving emptying the fuel tanks, opening access panels, purging with fresh air, and physically climbing into and visually inspecting the fuel tanks and/or sending probes and cameras further into hard to reach areas to check for corrosion at regular intervals. All these methods require substantial amounts of work and resources to implement and increase the amount of time the craft is unavailable for operations due to required maintenance to inspect for corrosion in fuel tanks.

Accordingly, there is a need for systems and methods for disinfecting fuel tanks that reduce microbial contamination while also reducing the need for fuel pre-treatment and/or maintenance services, such as draining and inspection, extend the life of fuel filters and screens, and increase the time a craft is available for operations.

BRIEF SUMMARY

This summary is intended merely to introduce a simplified summary of some aspects of one or more implementations of the present disclosure. This summary is not an extensive overview, nor is it intended to identify key or critical elements of the present teachings, nor to delineate the scope of the disclosure. Rather, its purpose is merely to present one or more concepts in simplified form as a prelude to the detailed description below.

The foregoing and/or other aspects and utilities exemplified in the present disclosure may be achieved by providing a fuel tank disinfection system, including one or more ultraviolet (UV) light emitters disposed within a fuel tank and configured to irradiate one or more water collecting areas within the fuel tank with UV light; and one or more UV light sensors disposed within the fuel tank and in proximity to the one or more water collecting areas and configured to measure the UV light irradiated on the one or more water collecting areas.

The one or more UV light emitters may irradiate predetermined areas within the fuel tank.

The one or more UV light emitters may be configured to irradiate substantially only the one or more water collecting areas.

The one or more UV light emitters may be configured to irradiate the one or more water collecting areas according to an irradiation profile.

The irradiation profile may correspond to UV light irradiation requirements to disinfect the one or more water collecting areas.

The irradiation profile may include at least one of a UV light radiation intensity and a UV light radiation time of exposure.

The one or more UV light sensors may confirm that the one or more water collecting areas are irradiated by the one or more UV light emitters according to the irradiation profile.

The one or more UV light sensors may generate an alert if the one or more UV light emitters irradiate the one or more water collecting areas outside the irradiation profile.

The one or more UV light sensors may measure at least one of a UV light intensity at the one or more water collecting areas and a UV light irradiation duration at the one or more the water collecting areas, and wherein the one or more UV light sensors generate an alert if at least one of the UV light intensity at the one or more water collecting areas and the UV light irradiation duration at the one or more the water collecting areas is outside the irradiation profile.

Each of the one or more water collecting areas may have at least one corresponding UV light sensor.

The one or more UV light sensors may be disposed within from about 2 inches to about 20 inches from the one or more water collecting areas.

The one or more UV light emitters may generate substantially no heat and substantially no electrical current within the fuel tank.

Each of the one or more UV light emitters may generate a UV light irradiation area from about 4 inches to about 20 inches in diameter at the one or more water collecting areas.

The UV light may have a wavelength from about 100 nanometers (nm) to about 280 nm.

The one or more UV light emitters may include one or more fiber optic cables.

The fuel tank disinfection system may further include a UV light source to provide a UV light to the one or more UV light emitters, and a power source to power at least one of the one or more UV light emitters, the one or more UV light sensors, and the UV light source, and at least one of the UV light source and the power source may be disposed outside of the fuel tank.

The fuel tank disinfection system may further include a controller configured to control at least one of the one or more UV light emitters, the one or more UV light sensors, the UV light source, and the power source, to irradiate the one or more water collecting areas according to the irradiation profile.

The fuel tank may be disposed within a craft, and at least one of the UV light source and the power source may be disposed outside of the craft.

The fuel tank disinfection system may not be operated during operation of the craft.

The foregoing and/or other aspects and utilities exemplified in the present disclosure may also be achieved by providing a method to disinfect a fuel tank, including placing one or more UV light sensors in proximity one or more water collecting areas within the fuel tank, placing one or more UV light emitters within the fuel tank to irradiate the one or more water collecting areas with UV light, irradiation the one or more water collecting areas; and controlling the UV light irradiation on the one or more water collecting areas.

The method may further include identifying one or more water collecting areas within a fuel tank.

Further areas of applicability will become apparent from the detailed description provided hereinafter. It should be understood that the detailed description and specific examples, while indicating the preferred embodiment of the invention, are intended for purposes of illustration only and are not intended to limit the scope of the invention.

BRIEF DESCRIPTION OF THE DRAWINGS

The accompanying drawings, which are incorporated in, and constitute a part of this specification, illustrate implementations of the present teachings and, together with the description, serve to explain the principles of the disclosure. In the figures.

Figure 1:
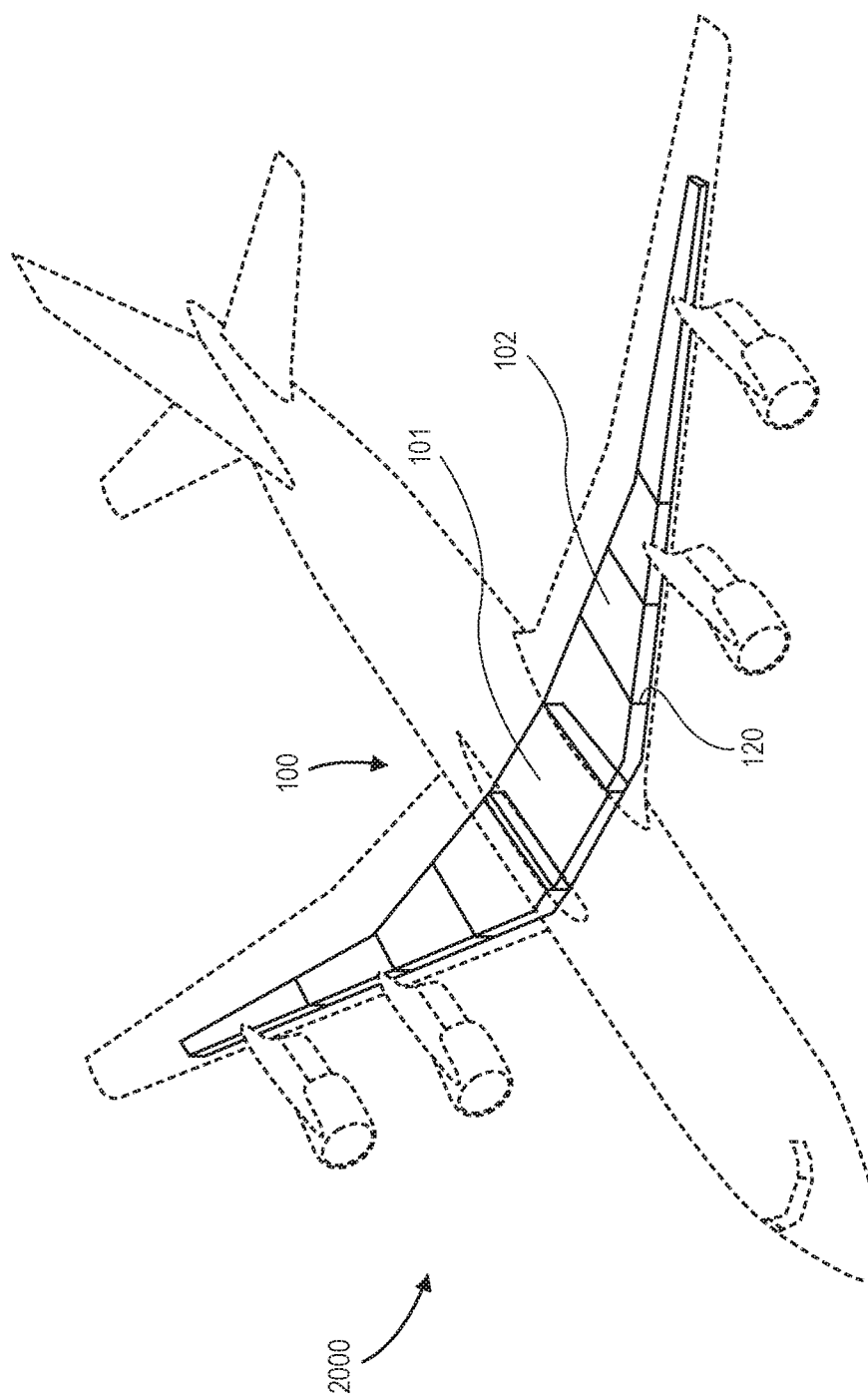
FIG. 1 illustrates an aircraft according to an implementation of the present disclosure.

It should be noted that some details of the figures have been simplified and are drawn to facilitate understanding of the present teachings rather than to maintain strict structural accuracy, detail, and scale.

DETAILED DESCRIPTION

Reference will now be made in detail to exemplary implementations of the present teachings, examples of which are illustrated in the accompanying drawings. Generally, the same reference numbers will be used throughout the drawings to refer to the same or like parts.

Throughout the specification and claims, the following terms take the meanings explicitly associated herein, unless the context clearly dictates otherwise. Phrases, such as, "in an implementation," "in certain implementations," and "in some implementations" as used herein do not necessarily refer to the same implementation(s), though they may. Furthermore, the phrases "in another implementation" and "in some other implementations" as used herein do not necessarily refer to a different implementation, although they may. As described below, various implementations can be readily combined, without departing from the scope or spirit of the present disclosure.

As used herein, the term "or" is an inclusive operator, and is equivalent to the term "and/or," unless the context clearly dictates otherwise. The term "based on" is not exclusive and allows for being based on additional factors not described, unless the context clearly dictates otherwise. In the specification, the recitation of "at least one of A, B, and C," includes implementations containing A, B, or C, multiple examples of A, B, or C, or combinations of A/B, A/C, B/C, A/B/B/B/B/C, A/B/C, etc. In addition, throughout the specification, the meaning of "a," "an," and "the" include plural references. The meaning of "in" includes "in" and "on." Similarly, implementations of the present disclosure may suitably comprise, consist of, or consist essentially of, the elements A, B, C, etc.

It will also be understood that, although the terms first, second, etc. can be used herein to describe various elements, these elements should not be limited by these terms. These terms are only used to distinguish one element from another. For example, a first object, component, or step could be termed a second object, component, or step, and, similarly, a second object, component, or step could be termed a first object, component, or step, without departing from the scope of the invention. The first object, component, or step, and the second object, component, or step, are both, objects, component, or steps, respectively, but they are not to be considered the same object, component, or step. It will be further understood that the terms "includes," "including," "comprises" and/or "comprising," when used in this specification, specify the presence of stated features, steps, operations, elements, and/or components, but do not preclude the presence or addition of one or more other features, steps, operations, elements, components, and/or groups thereof. Further, as used herein, the term "if" can be construed to mean "when" or "upon" or "in response to determining" or "in response to detecting," depending on the context.

All physical properties that are defined hereinafter are measured at 20° to 25° Celsius unless otherwise specified.

When referring to any numerical range of values herein, such ranges are understood to include each and every number and/or fraction between the stated range minimum and maximum, as well as the endpoints. For example, a range of 0.5% to 6% would expressly include all intermediate values of, for example, 0.6%, 0.7%, and 0.9%, all the way up to and including 5.95%, 5.97%, and 5.99%, among many others. The same applies to each other numerical property and/or elemental range set forth herein, unless the context clearly dictates otherwise.

Additionally, all numerical values are "about" or "approximately" the indicated value, and take into account experimental error and variations that would be expected by a person having ordinary skill in the art. It should be appreciated that all numerical values and ranges disclosed herein are approximate values and ranges. The terms "about" or "substantial" and "substantially" or "approximately," with reference to amounts or measurement values, are meant that the recited characteristic, parameter, or values need not be achieved exactly. Rather, deviations or variations, including, for example, tolerances, measurement error, measurement accuracy limitations, and other factors known to those skilled in the art, may occur in amounts that do not preclude the effect that the characteristic was intended to provide.

Unless otherwise specified, all percentages and amounts expressed herein and elsewhere in the specification should be understood to refer to percentages by weight. The percentages and amounts given are based on the active weight of the material. For example, for an active ingredient provided as a solution, the amounts given are based on the amount of the active ingredient without the amount of solvent or may be determined by weight loss after evaporation of the solvent.

With regard to procedures, methods, techniques, and workflows that are in accordance with some implementations, some operations in the procedures, methods, techniques, and workflows disclosed herein can be combined and/or the order of some operations can be changed.

Figure 2:
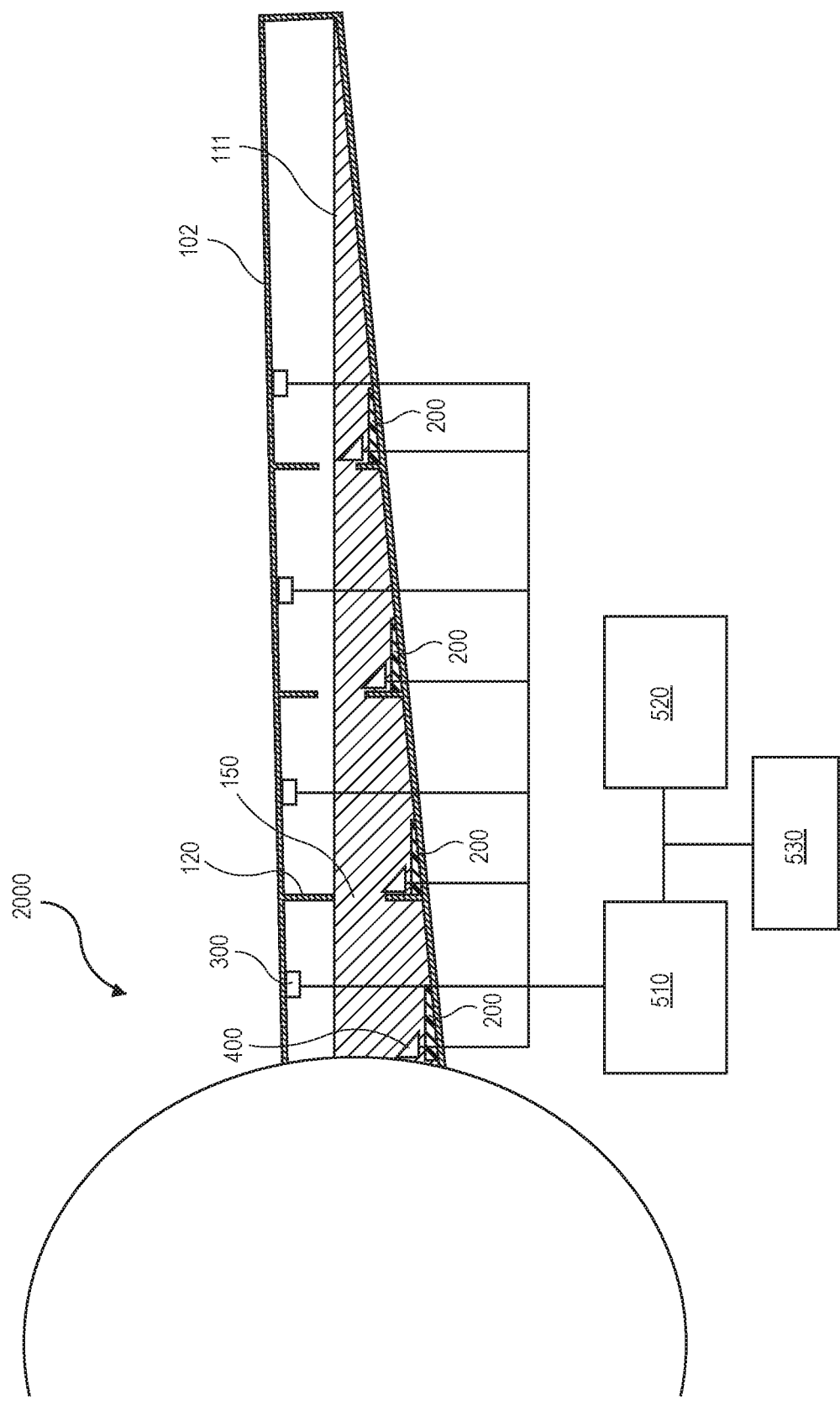
FIG. 2 illustrates a cross-section of a fuel tank for the aircraft of FIG. 1.
Figure 3:
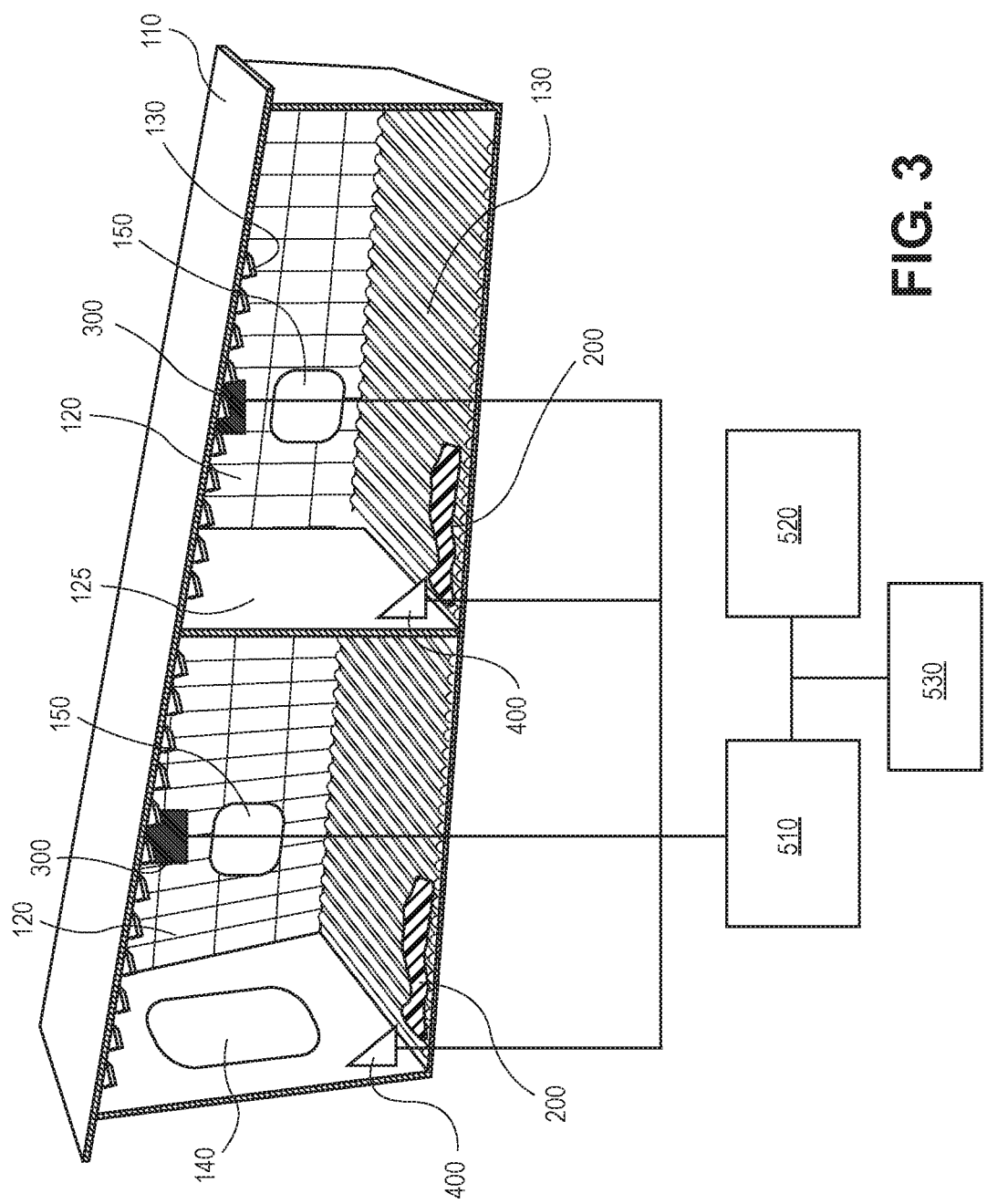
FIG. 3 illustrates a cross-section of the fuel tank for the aircraft of FIG. 1.

FIG. 1 illustrates an aircraft according to an implementation of the present disclosure. As illustrated in FIG. 1, an aircraft 2000 may include one or more fuel tanks 100. For example, the aircraft 2000 includes a center body tank 101 and one or more wing fuel tanks 102. FIGS. 2 and 3 illustrate cross-sections of a fuel tank for the aircraft of FIG. 1. In particular, FIGS. 2 and 3 illustrate cross-sections of a wing fuel tank 102.

The fuel tanks 100 may be integrally formed. That is, the fuel tanks 100 may be defined by areas within the structure of the aircraft 2000 that have been sealed to allow for fuel storage. For example, as illustrated in FIGS. 2-3, a wing fuel tank 102 includes aircraft skins 110, one or more ribs 120, one or more spars 125, one or more stringers 130, an access panel 140, and one or more ports 150 defining the wing fuel tank 102.

As illustrated in FIG. 2, the wing fuel tank 102 may be divided into sections by the one or more ribs 120. The ribs 120 may act as baffles to keep the fuel from sloshing. The one or more ports 150 may allow for liquid communication between the sections of the wing fuel tank 102. The wing fuel tank may also include a number of fuel valves, fuel pumps, fuel sensors, fuel drains, and fuel inlets (not illustrated) to manage a fuel flow in the wing fuel tanks 102 and the aircraft 2000. In addition, pipes, conduits, and wiring associated with other aircraft systems (not illustrated), such as electrical, hydraulic, and environmental systems, may also be present within the area defining the wing fuel tank 102.

While the present disclosure is described in terms of a wing fuel tank 102 of an aircraft 2000 as an example of a fuel tank 100, the present disclosure is not limited thereto. Implementations of the present disclosure may also be applied to other types of fuel tanks 100 and other types of craft. For example, the fuel tanks 100 can be implemented as rigid fuel tanks, removable fuel tanks, bladder fuel tanks, and tip fuel tanks. In addition, the fuel tanks 100 may be mounted on different types of craft, such as, but not limited to, unmanned air vehicles, rotorcraft, submarines, surface ships, as well as automobiles, tanks, trucks, power plants, and any other suitable type of objects.

As illustrated in FIGS. 2-3, the wing fuel tank 102 may include one or more water collecting areas 200.

As used herein, the term "water collecting areas" refers to areas within a fuel tank 100 where water may be trapped and/or collected. Water may collect underneath fuel 111 contained within the fuel tank 100. For example, water collecting areas 200 are low spots in the fuel tank 100, such as areas surrounding fuel drains or sump pumps. Water collecting areas 200 may also be areas with inadequate drainage or complicated geometries due to structural components of the aircraft or components of other aircraft systems. For example, water collecting areas 200 can exist at a low point next to a rib 120 defining a section of the fuel tank 100, such as the wing fuel tank 102 illustrated in FIG. 2.

Water collecting areas 200 can be identified by the presence of debris or bio-films associated with microbial contamination. For example, brown/black debris is often associated with the presence of bacteria or fungi, and mold, slim, or jelly-like films may often be observed in areas of the fuel tank where water collects.

In some implementations, water tends to collect at the same locations within a fuel tank. Accordingly, evidence of prior corrosion and/or microbial contamination can be used to identify water collecting areas 200 within a fuel tank 100.

In other implementations, water collecting areas 200 may be functionally discovered by filling a fuel tank 100 with a liquid and then taking particular note of areas with trapped liquid after the fuel tank 100 are emptied through normal fuel outlets, such as fuel supply and fuel/de-fuel connections.

Figure 4:
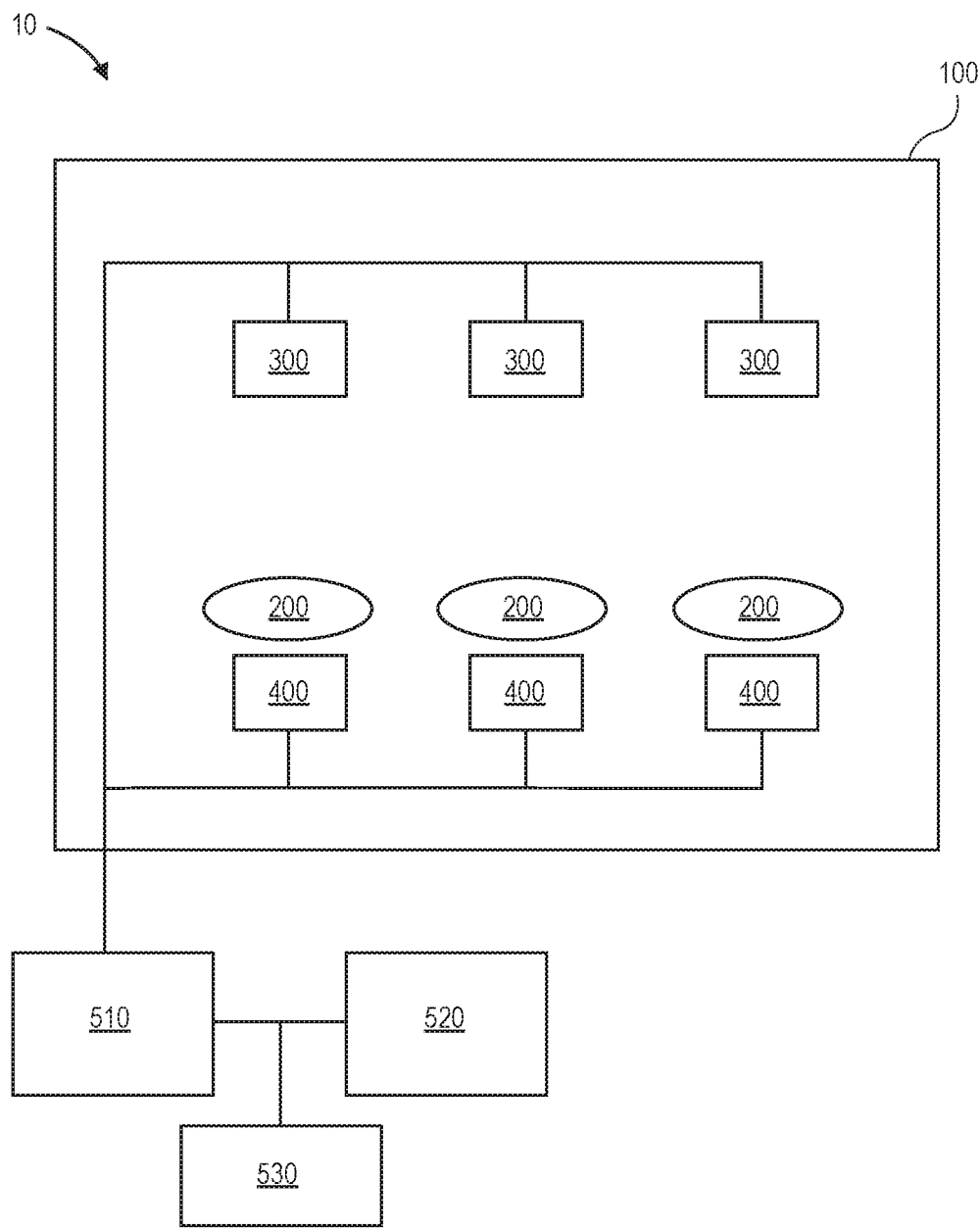
FIG. 4 illustrates a fuel tank disinfection system according to an implementation.

FIG. 4 illustrates a fuel tank disinfection system according to an implementation. As illustrated in FIG. 4, a fuel tank disinfection system 10 includes one or more ultraviolet (UV) light emitters 300 and one or more UV light sensors 400. The fuel tank disinfection system 10 also includes at least one of a UV light source 510, a power source 520, and a controller 530.

The one or more UV light emitters 300 can be disposed within the fuel tank 100. The one or more UV light emitters 300 are configured to irradiate one or more water collecting areas 200 within the fuel tank 100 with UV light.

The one or more UV light emitters 300 can be configured to irradiate substantially only the one or more water collecting areas 200. That is, the one or more UV light emitters 300 can be configured to irradiate predetermined areas within the fuel tank. For example, the one or more UV light emitters 300 irradiate a predetermined area surrounding the one or more water collecting areas 200. The one or more UV light emitters 300 can be configured not irradiate a substantial area within the fuel tank with UV light.

In order to limit the amount of energy used, or the exposure of areas within the fuel tank to UV light, the one or more UV light emitters 300 can generate a UV light irradiation area from about 4 inches to about 20 inches in diameter at the one or more water collecting areas 200. For example, the UV light emitters 300 generate a UV light irradiation area of 20 inches or less, 10 inches or less, or 5 inches or less. The UV light emitters 300 can generate a UV light irradiation area of 4 inches or more, 10 inches or more, or 15 inches or more.

The one or more UV light emitters 300 can be implemented as one or more light sources configured to emit UV radiation that can reduce or eliminate microorganisms, such as bacteria, molds, virus, and fungi. The UV radiation can be ultraviolet C (UVC) radiation. For example, a wavelength of the radiation is from about 100 nanometers (nm) to about 280 nm.

Accordingly, the one or more UV light emitters 300 can be configured to generate a UV light irradiation from about 100 nanometers (nm) to about 300 nm, which is known to inactivate or kill microorganisms. In other implementations, the one or more UV light emitters 300 may be configured to generate a UV light irradiation from about 100 nm to about 280 nm, from about 200 nm to about 280 nm, or from about 240 nanometers (nm) to about 280 nm.

The one or more UV light emitters 300 light can include one or more germicidal ultraviolet lamps. The one or more UV light emitters 300 light may include one or more UV light emitting diodes. In other implementations, the one or more UV light emitters 300 light include one or more fiber optic cables. For example, the one or more UV light emitters 300 include one or more hollow-core fiber optic cables.

In some implementations, a UV light source 510 and/or a power source 520 are placed outside of the fuel tank 100 and the one or more UV light emitters 300 are configured to generate substantially no heat within the fuel tank 100. For example, when the one or more UV light emitters 300 are implemented as one or more fiber optic cables configured to deliver the UV radiation, a UV light source 510 is outside the fuel tank 100 and the fiber optic cables delivers the UV light from the UV light source 510 to the water collecting areas 200 while generating substantially no heat and/or substantially no electrical current within the fuel tank 100.

The one or more UV light emitters 300 can be configured to irradiate the one or more water collecting areas 200 according to an irradiation profile. The irradiation profile determines the duration and/or the intensity of the UV light irradiation by the one or more UV light emitters 300. For example, the irradiation profile determines the time duration during which the UV light emitters are turned on or the intensity of UV light emitted by the one or more UV light emitters 300. The irradiation profile can correspond to at least one of environmental conditions and storage conditions associated with the fuel tank 100. For example, the irradiation profile is adjusted for humid environments or for longer term storage of fuel 111 in the fuel tank 100. In other implementations, the irradiation profile may be adjusted according to an operation profile for the craft incorporating the fuel tank 100. For example, an aircraft that is actively being flown and refueled may need a more active irradiation profile than an aircraft sitting on a ramp in active-ready-to-fly conditions. That is, a profile that irradiates the water collecting areas more often or at higher UV light intensities. However, refueling and then sitting for extended periods is when the greatest possibility may exist for water to enter and be trapped in the fuel tank 100. Accordingly, an irradiation profile can correspond to a maintenance profile, an operation profile, and/or a storage and refueling profile for the craft containing the fuel tank 100.

The irradiation profile can correspond to UV light irradiation requirements to disinfect the one or more water collecting areas 200. For example, the irradiation profile is configured to deliver an effective amount of UV radiation to disinfect the one or more water collecting areas 200. An effective amount of UV radiation may correspond to a reduction of microorganisms by 80% or more, by 90% or more, by 95% or more, or by 99% or more. Accordingly, the irradiation profile can be configured to reduce an amount of microorganisms in the water collecting areas 200 by 80% or more, by 90% or more, by 95% or more, or by 99% or more. The irradiation profile can be the same for all of the one or more water collecting areas 200 or the irradiation profile may vary for each of the one or more of the water collecting areas 200.

The irradiation profile can include at least one of a UV light radiation intensity and a UV light radiation time of exposure. Accordingly, an effective amount of UV light radiation can be achieved by increasing or adjusting the intensity of the ultraviolet radiation and/or the UV light radiation time of exposure.

For example, the irradiation profile can require that each of the one or more water collecting areas 200 be irradiated for from about 5 minutes to about 30 minutes every 10 to 30 days. In other implementations, the need for irradiation may be lower (lower humidity, less standing time), and the irradiation profile may require that each of the one or more water collecting areas 200 be irradiated for about 30 minutes after every refueling.

Similarly, the irradiation profile may require that each of the one or more water collecting areas 200 be irradiated at an intensity of ultraviolet radiation sufficient to reduce an amount of microorganisms in the water collecting areas 200 by 80% or more, by 90% or more, by 95% or more, or by 99% or more The one or more UV light sensors 400 are disposed within the fuel tank 100 and in proximity to the one or more water collecting areas 200. For example, each of the one or more water collecting areas 200 has at least one corresponding UV light sensor 400. The one or more UV light sensors 400 are disposed within from about 2 inches to about 20 inches from the one or more water collecting areas 200.

The one or more UV light sensors 400 can be configured to measure the UV light irradiated on the one or more water collecting areas 200. For example, the one or more UV light sensors 400 are configured to confirm that the one or more water collecting areas 200 are irradiated by the one or more UV light emitters 300 according to the irradiation profile. That is, the one or more UV light sensors 400 can be configured to detect at least one of a UV light radiation intensity and a UV light radiation time of exposure at the one or more water collecting areas 200. The information from the one or more UV light sensors 400 can be used to control the UV light sensors 400 according to the irradiation profile. That is, by using the one or more UV light sensors 400, the system 10 can be automated, and the system 10 can generate an alert and/or power off the one or more UV light emitters 300 when the one or more water collecting areas have been irradiated for a sufficiently effective time and/or intensity. In some implementations, the alert from the one or more UV light sensors 400 is transmitted to the controller 530 and the controller 530 powers off the UV light source 510 and/or the power source 520 to end the irradiation of the one or more water collecting areas 200.

The one or more UV light sensors 400 can generate an alert if the one or more UV light emitters 300 irradiate the one or more water collecting areas 200 outside the irradiation profile. For example, if a UV light radiation intensity and/or a UV light radiation time of exposure is less than required by the irradiation profile or if the UV light radiation intensity and/or a UV light radiation time of exposure has reached the level required by the irradiation profile. In some implementations, the alert from the one or more UV light sensors 400 is transmitted to the controller 530 and the controller 530 may adjust the UV light source 510 and/or the power source 520 to adjust the UV light radiation intensity and/or the UV light radiation time of exposure or the one or more UV light emitters 300.

The UV light source 510 is configured to provide a UV light to the one or more UV light emitters 300 and the one or more UV light emitters 300 are configured to transmit the UV light from the UV light source 510 to the one or more water collecting areas 200.

The power source 520 can be configured to power at least one of the one or more UV light emitters 300, the one or more UV light sensors 400, the UV light source 510, and the controller 530.

The controller 530 is configured to control at least one of the one or more UV light emitters 300, the one or more UV light sensors 400, the UV light source 510, and the power source 520. For example, the controller 530 is configured to control the one or more UV light emitter 300 and/or the UV light source 510 to irradiate the one or more water collecting areas 200 according to the irradiation profile. The controller 530 may be configured to control at least one of the one or more UV light emitters 300, the one or more UV light sensors 400, the UV light source 510, and the power source 520, to irradiate the one or more water collecting areas 200 according to the irradiation profile. The controller 530 may control each one of the one or more UV light emitters 300 separately to confirm that each of the one or more water collecting areas 200 is irradiated according to its corresponding irradiation profile.

The controller 530 can be configured to receive alerts generated by the UV light sensors and adjust the UV light radiation irradiated on the one or more water collecting areas 200. For example, the controller 530 increases or adjusts the intensity of the ultraviolet radiation and/or the UV light radiation time of exposure produced by the UV light source 510 and transmitted by the one or more UV light emitters 300, either together or individually, in response to an alert generated by one or more of the UV light sensors 400.

The controller 530 can record the UV light irradiated on the one or more UV light sensors 400. For example, the controller 530 creates a record of the UV light radiation intensity and UV light radiation time of exposure received at the one or more UV light sensors 400 for the fuel tank 100 or the craft containing the fuel tank 100. The record created by the controller 530 can be stored, printed, or reported, and can be used to generate an alert if it falls outside a required a maintenance profile.

In some implementations, in order to prevent exposing the interior of the fuel tank 100 to heat or electrical current, the fuel tank disinfection system 10 is designed to limit an amount of electrical current and/or heat within the fuel tank 100. For example, the one or more UV light emitters 300 is configured not to generate a UV light but instead transmit it from an external UV light source 510. Similarly, the one or more UV light emitters 300 and the one or more UV light sensors 400 can be configured to receive power only from an external power source 520. Accordingly, in some implementations, at least one of the UV light source 510, the power source 520, and the controller 530 are disposed outside of the fuel tank. In some implementation, where the fuel tank 100 is disposed within a craft, at least one of the UV light source 510, the power source 520, and the controller 530 are disposed outside of the craft.

Furthermore, the fuel tank disinfection system 10 can be configured to be ground operated. That is, to be operated only by ground crews during maintenance and not while the craft is in operation. Accordingly, the fuel tank disinfection system 10 can be configured to prevent its operation during operation of the craft. In one implementation, the fuel tank disinfection system 10 cannot be operated during operation of the craft.

Figure 5:
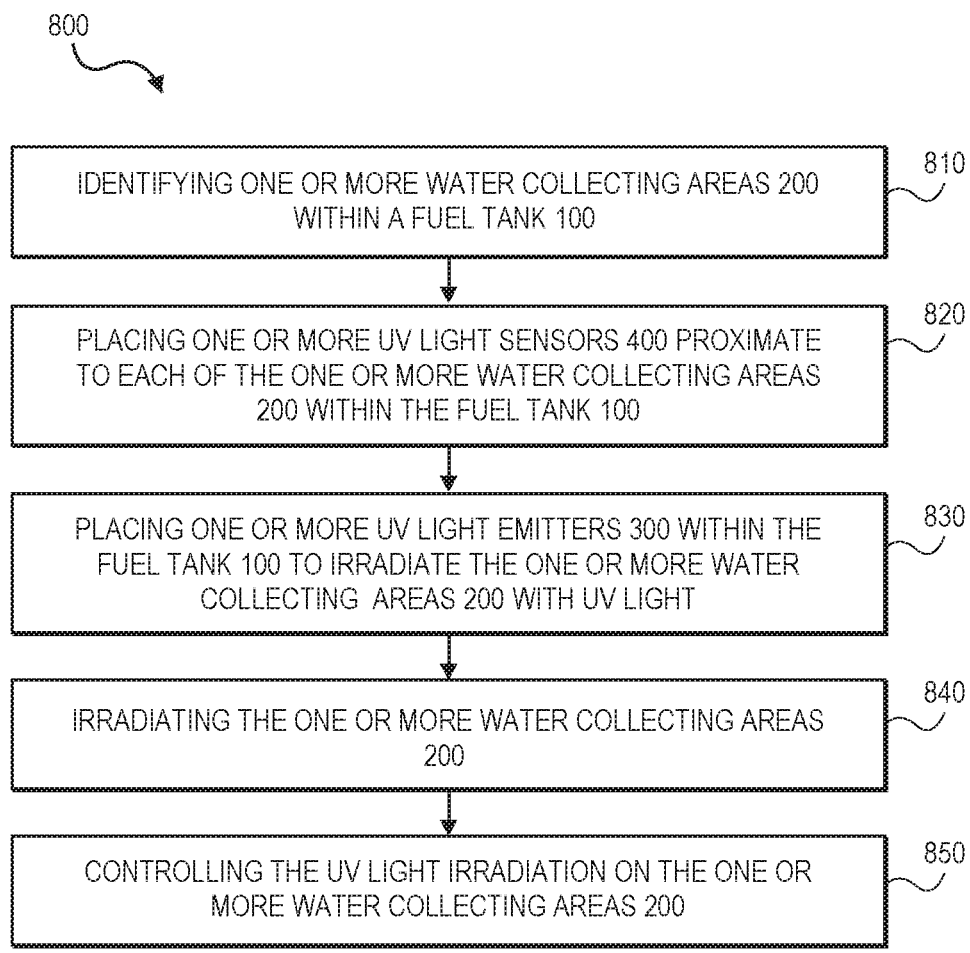
FIG. 5 illustrates a fuel tank disinfection method according to an implementation.

FIG. 5 illustrates a fuel tank disinfection method according to an implementation. As illustrated in FIG. 5, a method 800 can begin with identifying one or more water collecting areas 200 within a fuel tank 100 in operation 810. As described above, the water collecting areas 200 can correspond to low spots within the fuel tank 100 due to design features of the fuel tank 100 and/or may correspond to areas previously identified as collecting water and/or suffering from microbial contamination.

Operation 820 includes placing one or more UV light sensors 400 in proximity to each of the one or more water collecting areas 200 within the fuel tank 100. The UV light sensors 400 can be configured to measure at least one of a UV light radiation intensity and a UV light radiation time of exposure corresponding to the one or more water collecting areas 200.

Operation 830 include placing one or more UV light emitters 300 within the fuel tank 100 to irradiate the one or more water collecting areas 200 with UV light.

Operation 840 includes irradiating the one or more water collecting areas 200. For example, the one or more water collecting areas 200 are irradiated with UV light from the one or more UV light emitters 300 and/or a UV light source 510 according to an irradiation profile.

Operation 850 includes controlling the UV light irradiation on the one or more water collecting areas 200. For example, a controller 530 is configured to control the one or more UV light emitters 300 and/or a UV light source 510 to ensure that each of the one or more water collecting areas 200 is irradiated with UV light according to the irradiation profile. In some implementations, the one or more UV light sensors 400 may be configured to create an alert if the UV light radiation received is outside the irradiation profile, and the controller 530 can increase or adjust the intensity of the ultraviolet radiation and/or the UV light radiation time of exposure produced by the one or more UV light emitters 300 and/or the UV light source 510 and directed at the one or more water collecting areas 200, either together or individually, in response to the alert generated by one or more UV light sensors 400.

Figure 6:
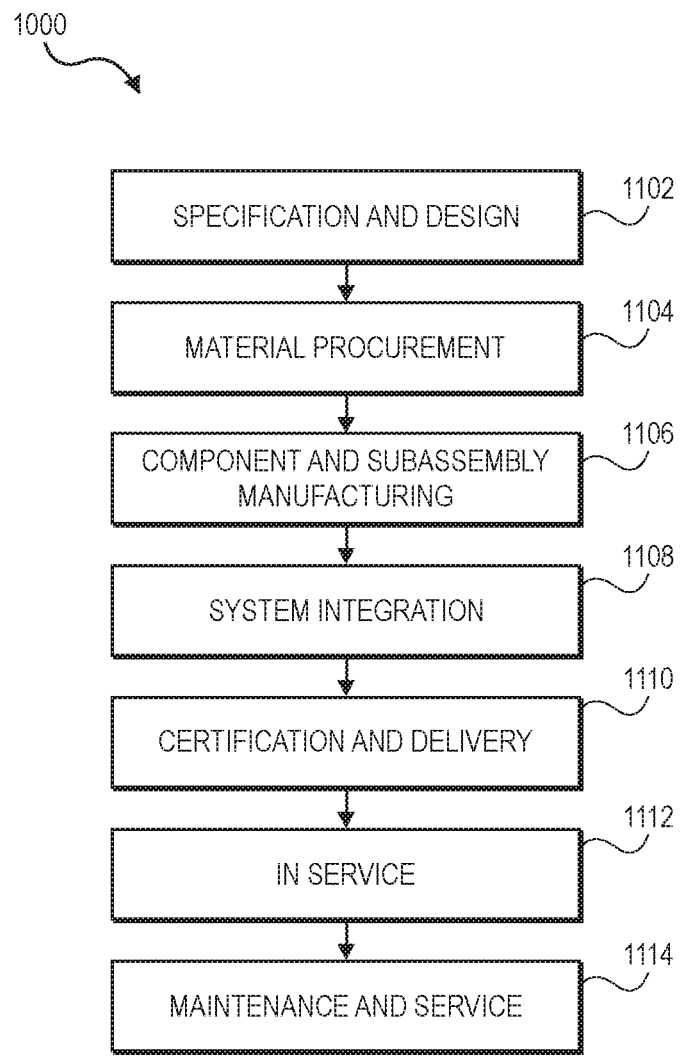
FIG. 6 illustrates a flow diagram of aircraft production and service methodology according to an implementation.
Figure 7:
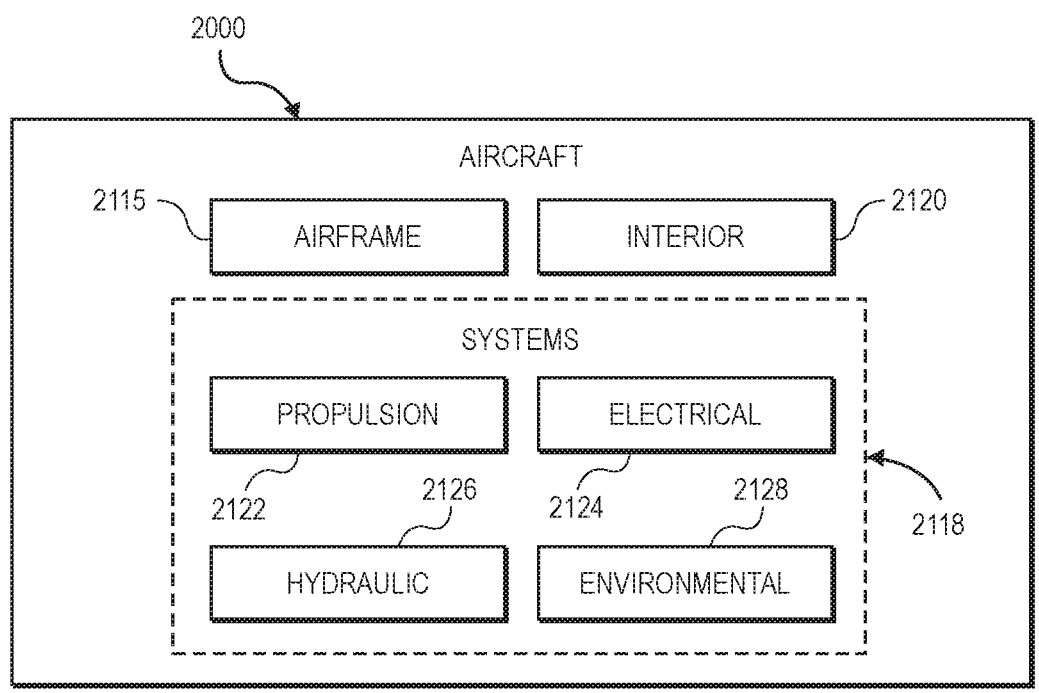
FIG. 7 illustrates a block diagram of an aircraft according to an implementation.

Implementations of the present disclosure may find use in a variety of potential applications, particularly in the transportation industry, including for example, aerospace, marine, automotive applications, and other application where fuel tank disinfection are desired. Thus, referring now to FIGS. 6 and 7, implementations of the disclosure can be used in the context of an aircraft manufacturing and service method 1000 as shown in FIG. 6 and an aircraft 2000 as shown in FIG. 7. During pre-production, exemplary method 1000 may include specification and design 1102 of the aircraft 2000 and material procurement 1104. During production, component and subassembly manufacturing 1106 and system integration 1108 of the aircraft 2000 takes place. Thereafter, the aircraft 2000 may go through certification and delivery 1110 in order to be placed in service 1112. While in service by a customer, the aircraft 2000 is scheduled for routine maintenance and service 1114, which may also include modification, reconfiguration, refurbishment, and so on.

Each of the processes of method 1000 may be performed or carried out by a system integrator, a third party, and/or an operator (e.g., a customer). For the purposes of this description, a system integrator may include without limitation any number of aircraft manufacturers and major-system subcontractors; a third party may include without limitation any number of vendors, subcontractors, and suppliers; and an operator may be an airline, leasing company, military entity, service organization, and so on.

As shown in FIG. 7, the aircraft 2000 produced by exemplary method 1000 can include an airframe 2115 with a plurality of systems 2118 and an interior 2120. Examples of systems 2118 include one or more of a propulsion system 2122, an electrical system 2124, a hydraulic system 2126, and an environmental system 2128. Any number of other systems may be included. Although an aerospace example is shown, the principles of the disclosure may be applied to other industries, such as the marine and automotive industries.

Systems and methods exemplified herein may be employed during any one or more of the stages of the aircraft manufacturing and service method 1000. For example, components or subassemblies corresponding to production process 1106 may be fabricated or manufactured in a manner similar to components or subassemblies produced while the aircraft 2000 is in service. Also, one or more apparatus examples, method examples, or a combination thereof may be utilized during the production stages 1106 and the 1108, for example, by substantially expediting assembly of or reducing the cost of an aircraft 2000. Similarly, one or more of apparatus examples, method examples, or a combination thereof may be utilized while the aircraft 2000 is in service, for example and without limitation, to maintenance and service 1114.

While FIGS. 6 and 7 describe the disclosure with respect to aircraft and aircraft manufacturing and servicing, the present disclosure is not limited thereto. The fuel disinfection systems and methods of the present disclosure may also be used for spacecraft, satellites, submarines, surface ships, automobiles, tanks, trucks, power plants, and any other suitable type of objects.

The present disclosure has been described with reference to exemplary implementations. Although a few implementations have been shown and described, it will be appreciated by those skilled in the art that changes may be made in these implementations without departing from the principles and spirit of preceding detailed description. It is intended that the present disclosure be construed as including all such modifications and alterations insofar as they come within the scope of the appended claims or the equivalents thereof.

What is claimed, is:

1. A fuel tank disinfection system, comprising:
   a fuel tank disposed within a craft to store and supply fuel to the craft;
   one or more water collecting areas comprising low spots in the fuel tank where water can collect underneath fuel contained within the fuel tank;
   one or more ultraviolet (UV) light emitters disposed within the fuel tank to irradiate the one or more water collecting areas with UV light and deliver an effective amount of UV radiation to disinfect the one or more water collecting areas; and
   one or more UV light sensors disposed within the fuel tank and in proximity to the one or more water collecting areas to measure the UV light irradiated on the one or more water collecting areas.

2. The fuel tank disinfection system of claim 1, wherein the fuel tank is integrally formed within a structure of the craft, and wherein the one or more UV light emitters irradiate predetermined areas within the fuel tank.

3. The fuel tank disinfection system of claim 1, wherein the one or more UV light emitters irradiate substantially only the one or more water collecting areas.

4. The fuel tank disinfection system of claim 1, wherein the one or more UV light emitters irradiate the one or more water collecting areas according to an irradiation profile.

5. The fuel tank disinfection system of claim 4, wherein the irradiation profile corresponds to UV light irradiation requirements to deliver an effective amount of UV radiation to disinfect the one or more water collecting areas.

6. The fuel tank disinfection system of claim 4, wherein the irradiation profile includes at least one of a UV light radiation intensity and a UV light radiation time of exposure.

7. The fuel tank disinfection system of claim 4, wherein the one or more UV light sensors confirm that the one or more water collecting areas are irradiated by the one or more UV light emitters according to the irradiation profile.

8. The fuel tank disinfection system of claim 7, wherein the one or more UV light sensors measure at least one of a UV light intensity at the one or more water collecting areas and a UV light irradiation duration at the one or more the water collecting areas, and wherein the one or more UV light sensors generate an alert if at least one of the UV light intensity at the one or more water collecting areas and the UV light irradiation duration at the one or more the water collecting areas is outside the irradiation profile.

9. The fuel tank disinfection system of claim 4, wherein the one or more UV light sensors generate an alert if the one or more UV light emitters irradiate the one or more water collecting areas outside the irradiation profile.

10. The fuel tank disinfection system of claim 4, further comprising: a UV light source to provide a UV light to the one or more UV light emitters, and a power source to power at least one of the one or more UV light emitters, the one or more UV light sensors, and the UV light source, wherein at least one of the UV light source and the power source are disposed outside of the fuel tank.

11. The fuel tank disinfection system of claim 10, further comprising: a controller to control at least one of the one or more UV light emitters, the one or more UV light sensors, the UV light source, and the power source, to irradiate the one or more water collecting areas according to the irradiation profile.

12. The fuel tank disinfection system of claim 11, wherein the fuel tank is disposed within a craft, and at least one of the UV light source and the power source is disposed outside of the craft.

13. The fuel tank disinfection system of claim 12, wherein the fuel tank disinfection system cannot be operated during operation of the craft.

14. The fuel tank disinfection system of claim 1, wherein each of the one or more water collecting areas has at least one corresponding UV light sensor.

15. The fuel tank disinfection system of claim 1, wherein the one or more UV light sensors are disposed within from about 2 inches to about 20 inches from the one or more water collecting areas.

16. The fuel tank disinfection system of claim 1, wherein the one or more UV light emitters generates substantially no heat and substantially no electrical current within the fuel tank.

17. The fuel tank disinfection system of claim 1, wherein each of the one or more UV light emitters generates a UV light irradiation area from about 4 inches to about 20 inches in diameter at the one or more water collecting areas.

18. The fuel tank disinfection system of claim 1, wherein the UV light has a wavelength from about 100 nanometers (nm) to about 280 nm.

19. The fuel tank disinfection system of claim 1, wherein the one or more UV light emitters comprise one or more fiber optic cables.

20. The fuel tank disinfection system of claim 1, wherein the one or more UV light emitters comprise one or more germicidal ultraviolet lamps.

21. A method to disinfect a fuel tank disposed within a craft to store and supply fuel to the craft, comprising: identifying one or more water collecting areas comprising low spots in the fuel tank where water can collect underneath fuel contained within the fuel tank; placing one or more UV light sensors in proximity to the one or more water collecting areas within the fuel tank; placing one or more UV light emitters within the fuel tank to irradiate the one or more water collecting areas with UV light; irradiation the one or more water collecting areas; and controlling the UV light irradiation on the one or more water collecting areas to deliver an effective amount of UV radiation to disinfect the one or more water collecting areas.

* * * * *